US007150766B2

(12) United States Patent
Hanna et al.

(10) Patent No.: US 7,150,766 B2
(45) Date of Patent: *Dec. 19, 2006

(54) METHOD OF PARTICLE FORMATION (75) Inventors: Mazen H. Hanna, Bradford (GB); Peter York, Ilkley (GB)

(73) Assignee: Nektar Therapeutics UK, Ltd., Bradford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/006,464

(22) Filed: Dec. 7, 2004

(65) Prior Publication Data

US 2005/0206023 A1  Sep. 22, 2005

Related U.S. Application Data (63) Continuation of application No. 10/030,392, filed as application No. PCT/GB00/02606 on Jul. 7, 2000, now Pat. No. 6,860,907.

(30) Foreign Application Priority Data

Aug. 7, 1999 (GB) .................................... 9915975

(51) Int. Cl.
B01D 9/00 (2006.01)

(52) U.S. Cl. .......................................... 23/300; 23/296

(58) Field of Classification Search .................. 23/300, 23/301, 296
See application file for complete search history.

(56) References Cited

U.S. PATENT DOCUMENTS

| | | |
|---|---|---|
| 4,328,107 A | 5/1982 | Wright |
| 4,361,285 A | 11/1982 | Koppehele et al. |
| 4,582,731 A | 4/1986 | Smith |
| 4,702,799 A | 10/1987 | Tuot |
| 4,737,384 A | 4/1988 | Murthy et al. |
| 4,919,853 A | 4/1990 | Alvarez et al. |
| 4,923,720 A | 5/1990 | Lee et al. |
| 4,970,093 A | 11/1990 | Sievers et al. |
| 4,977,785 A | 12/1990 | Willoughby et al. |
| 5,009,367 A | 4/1991 | Nielsen |
| 5,043,280 A | 8/1991 | Fischer et al. |
| 5,106,659 A | 4/1992 | Hastings et al. |
| 5,221,731 A | 6/1993 | Weymans et al. |
| 5,229,486 A | 7/1993 | Paul et al. |
| 5,264,536 A | 11/1993 | Radosz |
| 5,437,798 A | 8/1995 | LaRoche et al. |
| 5,548,004 A | 8/1996 | Mandel et al. |
| 5,554,382 A | 9/1996 | Castor |
| 5,639,441 A | 6/1997 | Sievers et al. |
| 5,707,634 A | 1/1998 | Schmitt |
| 5,708,039 A | 1/1998 | Daly et al. |
| 5,716,558 A | 2/1998 | Nielsen et al. |
| 5,833,891 A | 11/1998 | Subramaniam et al. |
| 5,981,474 A | 11/1999 | Manning et al. |
| 6,063,910 A | 5/2000 | Debenedetti et al. |
| 6,860,907 B1 * | 3/2005 | Hanna et al. ............... 23/300 |

FOREIGN PATENT DOCUMENTS

| | | |
|---|---|---|
| DE | 1078283 | 3/1960 |
| DE | 4041563 | 6/1992 |
| EP | 322687 | 5/1993 |
| EP | 542314 | 5/1993 |
| GB | 2322326 | 8/1998 |
| JP | 1-176437 | 7/1989 |
| JP | 5-57166 | 3/1993 |
| WO | 90/03782 | 4/1990 |
| WO | 90/11139 | 10/1990 |
| WO | 95/01221 | 1/1995 |
| WO | WO 9501324 A1 * | 1/1995 |
| WO | 95/21688 | 8/1995 |
| WO | 96/00610 | 1/1996 |
| WO | 97/31691 | 9/1997 |
| WO | 99/44733 | 9/1999 |
| WO | 99/59710 | 11/1999 |

OTHER PUBLICATIONS

Barj et al, "Submicronic MgAl2O4 Powder Synthesis in Supercritical Ethanol," J. of Materials Sci., No. 27 p. 2187-2192, (1992), no month.

Bleich et al., "Aerosol Solvent Extraction System—A New Microparticle Production Technique," International J. of Pharmaceutics, 97:111-117, (1993), no month.

Bodmeier et al., "Polymeric Microspheres Prepared by Spraying Into Compressed Carbon Dioxide," Pharmaceutical Research, 12(8):1211-1217, (1995), no month.

(Continued)

Primary Examiner—Edward M. Johnson
(74) Attorney, Agent, or Firm—Patterson & Sheridan, LLP (57) ABSTRACT The invention provides a method for forming particles of a target substance, comprising (a) co-introducing into a particle formation vessel, under controlled temperature and pressure, a supercritical or near-critical anti-solvent fluid; a first target substance in a first vehicle; and a second target substance in a second vehicle; and (b) using the anti-solvent to disperse the target substances in their respective vehicles and to extract the vehicles, substantially simultaneously and substantially immediately on introduction of the fluids into the particle formation vessel. The second vehicle is immiscible with the first, and contact between the first and second vehicles occurs a sufficiently short period of time before their dispersion by the anti-solvent, and with sufficient physical mixing, as to allow only insignificant, if any, phase separation to occur between the two vehicles between their contact with one another and their dispersion.

9 Claims, 10 Drawing Sheets

OTHER PUBLICATIONS

Chang et al., "Separation of B-Carotene Mixtures Precipitated from Liquid Solvents with High-Pressure CO2," Biotechnol. Prog., No. 7, p. 275-278, (1991), no month.

Chang et al., "Precipitation of Microsize Organic Particles from Supercritical Fluids," AIChE Journal, 35(11):1876-1882, (Nov. 1989).

Chen et al., "Supercritical Antisolvent Fractionation of Polyethylene Simulated with Multistage Algorithm and SAFTEquation of State: Staging Leads to High Selectivity Enhancements for Light Fractions," Ind. Eng. Chem. Res., 33:306-310, (1994), no month.

Chhor et al., "Synthesis of Submicron TIO2 Powders in Vapor, Liquid and Supercritical Phases, a Comparative Study," Materials Chemistry and Physics, 32:249-254, (1992), no month.

Cygnarowicz et al., "Design and Control of a Process to Extract B-Carotene with Supercritical Carbon Dioxide," Biotechnol. Prog., 6:82-91, (1990), no month.

Debenedetti et al., "Application of Supercritical Fluids for the Production of Sustained Delivery Devices," J. Cont. Rel, No. 24, p. 27-44, (1993), no month.

Debenedetti et al., "Rapid Expansion of Supercritical Solutions (RESS): Fundamentals and Applications," Fluid Phase Equilibria, 82:311-321, (1993), no month.

Debenedetti et al., "Supercritical Fluids: A New Medium for the Formation of Particles of Biomedical Interest," Proceed. Intern. Symp. Control Rel. Bioact. Mater., 20, p. 141-142, (1993), no month.

Dill et al., "Denatured States of Proteins," Annu. Rev. Biochem, No. 60, p. 795-825, (1991), no month.

Dixon et al., "Polymeric Materials Formed by Precipitation with a Compressed Fluid Antisolvent," AIChE J., 39 (1):127-139, (1993), no month.

Donsi et al., "Micronization by Means of Supercritical Fluids: Possibility of Application to Pharmaceutical Field," Pharm. ACTA HELV. 66, Nr. 5-6, p. 170-173, (1991), no month.

Francis, "Ternary Systems of Liquid Carbon Dioixide," J. of Physical Chemistry, 58:1099-1114, (1954), no month.

Gallagher et al., "Gas Anti-Solvent Recrystallization of RDX: Formation of Ultra-fine Particles of a Difficult-to-Comminute Explosive," The J. of Supercritical Fluids, No. 5, p. 130-142, (1992), no month.

Gallagher et al., "Gas AntiSolvent Recrystallization: New Process to Recrystallize Compounds Insoluble in Supercritical Fluids," ACS Symp. Ser. No. 406, p. 334-354, (1989), no month.

Julienne et al., "Preparation of Poly (D, L-Lactide/Glycolide) Nanoparticles of Controlled Particle Size Distribution: Application of Experimental Designs," Drug Development and Industrial Pharmacy, 18(10):1063-1077, (1992), no month.

Jung et al., "Particle Design Using Supercritical Fluids: Literature and Patent Survey," J. of Supercritical Fluids, 20:179-219, (2001), no month.

Lahiere et al., "Mass-Transfer Efficiencies of Column Contactors in Supercritical Extraction Service," Ind. Eng. Chem. Res. No. 26, p. 2086-2092, (1987), no month.

Larson et al., "Evaluation of Supercritical Fluid Extraction in the Pharmaceutical Industry," Biotech. Progress, 2(2):73-82, (1986), no month.

Loth et al., "Properties and Dissolution of Drugs Micronized by Crystallization from Supercritical Gases," International J. of Pharmaceuticals, 32:265-267, (1986), no month.

Matson et al., "Production of Powders and Films by the Rapid Expansion of Supercritical Solutions," J. of Materials Science, No. 22, p. 1919-1928, (1987), no month.

Matson et al., "Rapid Expansion of Supercritical Fluid Solutions: Solute Formation of Powders, Thin Films and Fibers," Ind. Eng. Chem Res., 26:2298-2306, (1987), no month.

Mohamed et al., "Solids Formation After the Expansion of Supercritical Mixtures," Supercritical Fluid Science and Technology, Chapter 23, American Chemical Society, p. 355-378, (1989), no month.

O'Callaghan et al., "Novel Method for Detection of (B)-Lactamases by Using a Chromogenic Cephalosporin Substrate," Antimicrobial Agents and Chemotherapy, 1(4):283-288, (1972), no month.

Phillips et al, "Rapid Expansion from Supercritical Solutions: Application to Pharmaceutical Processes," International J. of Pharmaceutics, 94:1-10, (1993), no month.

Randolph et al., "Sub-Micrometer-Sized Biodegradable Particles of Poly (L-Lactic Acid) via the Gas Antisolvent Spray Precipitation Process," Biotechnol. Prog, 9(4):429-435, (1993), no month.

Sanchez et al., "Development of Biodegradable Microspheres and Nanospheres for the Controlled Release of Cyclosporin A," International J. of Pharmaceutics, 99:263-273, (1993), no month.

Stahl et al., "Dense Gas Extraction on a Laboratory Scale: A Survey of Some Recent Results," Fluid Phase Equilibria, No. 10, p. 269-278, (1983), no month.

Stengers et al., "Carbon Dioxide at its Critical State," Chemical & Engineering News, Jun. 10, 1968.

Tom et al., "Applications of Supercritical Fluids in the Controlled Release of Drugs," ACS Symposium Series, Supercritical Fluid Engineering Science Fundamentals and Applications, Chpt. 19, p. 238-257, (1993), no month.

Tom et al., "Formation of Bioerodible Polymeric Microspheres and Microparticles by Rapid Expansion of Supercritical Solutions," Biotechnol. Prog., 7:403-411, (1991), no month.

Tom et al., "Particle Formation with Supercritical Fluids—A Review," J. Aerosol Sci., 1st Ed., 22(5):555-584, (1981), no month.

Ullmans Encyclopedia of Industrial Chemistry, vol. B2, Fifth Ed., title page, copyright page, and p. 7-21 and 7-22, (1988), no month.

Yeo et al., "Formation of Microparticulate Protein Powders Using a Supercritical Fluid Antisolvent," Biotechnology and Bioengineering, 41:341-346, (1993), no month.

* cited by examiner

METHOD OF PARTICLE FORMATION

RELATIONSHIP TO OTHER APPLICATIONS

This application is a continuation of U.S. Application Ser. No. 10/030,392, filed 6$^{th}$Jun. 2002, now U.S. Pat. No. 6/860,907 which was a 371 application of PCT GB/00/02606, filed 7$^{th}$Jul. 2000, which claims the benefit of U.K. application GB 9915975 filed 7$^{th}$Aug. 1999.

FIELD OF THE INVENTION

This invention relates to a method for the formation of particles of a target substance, using a supercritical or near-critical fluid as an anti-solvent.

BACKGROUND TO THE INVENTION

Methods are already known in which a supercritical fluid is used as an anti-solvent to precipitate particles of a substance of interest from solution or suspension. One such method is known as "SEDS"™ ("Solution Enhanced Dispersion by Supercritical fluids") and is disclosed in WO-95/01221. In SEDS™, a target substance is dissolved or suspended in an appropriate vehicle, and the solution or suspension then co-introduced into a particle formation vessel with a supercritical anti-solvent fluid in which the vehicle is soluble. The co-introduction is effected in a particular way, to ensure that:

both the solution/suspension and the supercritical fluid enter the vessel at substantially the same point, which is also the same or substantially the same as the point where they meet; and in the region where the fluids meet and enter the vessel, the mechanical energy of the supercritical fluid serves to disperse the solution/suspension (ie, to break it up into individual fluid elements) at the same time as the supercritical fluid extracts the vehicle so as to cause particle formation.

Thus, in SEDS™, the supercritical fluid serves not only as an anti-solvent but also as a mechanical dispersing agent. The simultaneity of fluid contact, dispersion and particle formation provides a high degree of control over the physicochemical properties of the particulate product.

One particular embodiment of SEDS™ is described in WO-96/00610. The target substance is dissolved or suspended in a first vehicle, and the solution/suspension is then contacted, either at or immediately prior to its contact with the co-introduced anti-solvent, with a second vehicle. The second vehicle must be soluble in the anti-solvent but the first need not be, since both vehicles are extracted together into the anti-solvent. This embodiment widens the applicability of the basic SEDS™ technique to further target substances and vehicles: a first vehicle may be used which would not otherwise be extractable into the chosen anti-solvent but which is compatible with the target substance, and a second vehicle may be used which, although extractable into the anti-solvent, is less compatible with the target substance.

The method disclosed in WO-96/00610 requires the first and second vehicles to be miscible with one another, preferably in all proportions. This naturally constrains the choice of vehicle pairs available for use with any given target substance and anti-solvent.

The present invention aims to provide an alternative method for particle formation, embodiments of which can be used to widen the choice of useable target substance/vehicle/anti-solvent combinations.

STATEMENTS OF THE INVENTION

According to the present invention there is provided a method for forming particles of a target substance, the method comprising (a) co-introducing into a particle formation vessel, the temperature and pressure in which are controlled, an anti-solvent fluid which is either a supercritical or a near-critical fluid; a solution or suspension of the target substance in a first vehicle (the "target solution/suspension"); and a second vehicle which is soluble or substantially soluble in the anti-solvent fluid; and (b) using the anti-solvent fluid to disperse the target solution/suspension and the second vehicle, and to extract the vehicles, substantially simultaneously and substantially immediately on introduction of the fluids into the particle formation vessel, wherein the second vehicle is immiscible with the first vehicle, and wherein contact between the target solution/suspension and the second vehicle occurs a sufficiently short period of time before their dispersion by the anti-solvent fluid, and with sufficient physical mixing, as to allow only insignificant, if any, phase separation to occur between the two vehicles between their contact with one another and their dispersion.

Ideally, contact between the target solution/suspension and the second vehicle occurs either substantially simultaneously with, or immediately before, dispersion of the two vehicles by the anti-solvent fluid.

The method of the present invention is therefore a modified version of that disclosed in WO-96/00610. However, whereas WO-96/00610 emphasises throughout that the first and second vehicles should be miscible with one another, in order that both may be extracted into the anti-solvent together, we have now surprisingly found that immiscible vehicle pairs may be used in an analogous fashion, and can still be extracted together into a suitable supercritical or near-critical anti-solvent. Other prior art particle formation techniques which make use of supercritical or near-critical fluid anti-solvents also fail to recognise that immiscible vehicles may be paired together.

The invention can thus widen the choice of vehicle pairs available for any given target substance(s) and anti-solvent in a SEDS™ process. In addition, it can help to reduce or eliminate so-called solvent/anti-solvent effects that can arise when using two vehicles together. A given target substance may, for instance, be highly soluble in the first vehicle but only sparingly soluble in the second. The immiscibility of the two vehicles, in the method of the present invention, means that the second cannot to any significant degree act as an anti-solvent for the target substance, thus avoiding nucleation of the target prior to contact with the anti-solvent fluid (which might otherwise take place upstream of the particle formation vessel, causing apparatus blockages).

Contact between the target solution/suspension and the second vehicle must not occur too long before they contact the anti-solvent fluid, otherwise the two immiscible vehicles can separate into distinct phases leading to inhomogeneous fluid flows and loss of control over the particle formation process. Any such phase separation should be on a sufficiently small scale, and occur for a sufficiently short period of time, that the anti-solvent still in effect (ie, under the timescales used) disperses a uniform mixture of the target solution/suspension and the second vehicle. Thus, the contact preferably occurs either within the fluid inlet means (such as a nozzle) used to introduce the fluids into the particle formation vessel, or at or immediately before the point of entry of the vehicles into the inlet means. More preferably contact occurs within the fluid inlet means, even more preferably at or near its outlet.

The term "immiscible", as used herein, means that the two fluids are not, in at least some relative proportions, miscible with one another, ie, in at least some proportions they will form a two-phase rather than a single-phase mixture (given an appropriate amount of standing time). The solubility of the first vehicle in the second may for instance be 5% v/v or lower, even 1% v/v or lower. The two vehicles may be immiscible in all proportions, or in substantially all proportions for instance at first:second vehicle molar ratios lower than 40:60 or lower than 20:80 or lower than 15:85 or lower than 10:90. They may be immiscible, possibly in all proportions, at normal room temperature and pressure.

The term "substantially", when applied to a condition, is meant to encompass the exact condition (eg, exact simultaneity) as well as conditions which are (for practical purposes, taking into account the degree of precision with which such conditions can be measured and achieved) close to that exact condition, and/or which are similar enough to that exact condition as to achieve, in context, the same or a very similar effect.

In particular, the term "substantially soluble", as it relates to the second vehicle and the anti-solvent fluid, encompasses the situations where the former is very soluble or freely soluble in the latter (these terms being analogous to those defined in the British Pharmacopoeia 1999, Volume 1, pages 11 and 21, although under the relevant operating conditions). The requirement for the second vehicle to be soluble or substantially soluble in the anti-solvent fluid may alternatively be seen as a requirement for the two fluids to be miscible or substantially miscible with one another. By "miscible" is meant that the two fluids are miscible in all proportions, and "substantially miscible" encompasses the situation where the fluids can mix sufficiently well, under the operating conditions used, as to achieve the same or a similar effect, ie, dissolution of the fluids in one another and precipitation of the target substance.

"Substantially simultaneously" and "substantially immediately", referring to the timing of fluid contact events, imply sufficiently small time intervals (for instance, between the anti-solvent fluid contacting the vehicles, and the fluids entering the particle formation vessel) as preferably to eliminate, or substantially eliminate, the risk of particle formation occurring upstream of the particle formation vessel. The timing of the contact between the target solution/suspension and the second vehicle, relative to that of their dispersion by the anti-solvent fluid, will depend on the nature of the fluids (in particular the degree of immiscibility of the two vehicles), the target substance and the desired end product, as well as on the size and geometry of the particle formation vessel and the fluid inlet means and on the fluid flow rates. The contact may occur within about 0.001–10 seconds, more preferably within about 0.01–5 seconds, most preferably within about 0.01–1 second, of the dispersion.

"Substantially polar" encompasses polarities of 3 or higher, preferably 4 or higher, more preferably 5 or higher (see "Burdick & Jackson Solvent Guide, 3rd Edn", Burdick & Jackson, Michigan USA, 1990). "Substantially non-polar" encompasses polarities of less than 3, preferably 2 or less, more preferably 1 or less.

All references to solubilities, miscibilities and polarities are to the relevant fluid characteristics under the operating conditions used, ie, under the chosen conditions of temperature and pressure and taking into account any modifiers present in the fluids.

As used herein, the term "supercritical fluid" means a fluid at or above its critical pressure ($P_c$) and critical temperature ($T_c$) simultaneously. In practice, the pressure of the fluid is likely to be in the range (1.01–9.0)$P_c$, preferably (1.01–7.0)$P_c$, and its temperature in the range (1.01–4.0)$T_c$ (measured in Kelvin). However, some fluids (eg, helium and neon) have particularly low critical pressures and temperatures, and may need to be used under operating conditions well in excess of (such as up to 200 times) those critical values.

The term "near-critical fluid" encompasses both high pressure liquids, which are fluids at or above their critical pressure but below (although preferably close to) their critical temperature, and dense vapours, which are fluids at or above their critical temperature but below (although preferably close to) their critical pressure.

By way of example, a high pressure liquid might have a pressure between about 1.01 and 9 times its $P_c$, and a temperature between about 0.5 and 0.99 times its $T_c$. A dense vapour might, correspondingly, have a pressure between about 0.5 and 0.99 times its $P_c$, and a temperature between about 1.01 and 4 times its $T_c$.

The terms "supercritical fluid" and "near-critical fluid" each encompass a mixture of fluid types, so long as the mixture is in the supercritical or near-critical state respectively.

The term "vehicle" means a fluid which is able to carry a solid or solids in solution or suspension. A vehicle may be composed of one or more component fluids, eg, it may be a mixture of two or more solvents. Both first and second vehicles may be soluble (or substantially soluble) in the chosen anti-solvent fluid, although it is only essential that the second vehicle has this characteristic. Either vehicle may contain, in solution or suspension, other materials apart from the target substance.

The terms "supercritical solution" and "near-critical solution" mean respectively a supercritical or a near-critical fluid together with one or more vehicles which it has extracted and dissolved. The solution should itself still be in the supercritical or near-critical state, as the case may be, and as a single phase, at least within the particle formation vessel.

The terms "disperse" and "dispersion" refer generally to the transfer of kinetic energy from one fluid to another. They usually imply the formation of droplets, or of other analogous fluid elements, of the fluid to which the kinetic energy is transferred, typically of the target solution/suspension and/or of a vehicle.

The present invention relies on the mixing of the target solution/suspension, before or substantially simultaneously with its dispersion by the anti-solvent fluid, with a second vehicle specially chosen to be soluble in, or miscible with, the anti-solvent. On contact with the anti-solvent, the first vehicle is able to dissolve into the anti-solvent with the second vehicle, even if the first vehicle is not itself soluble in the anti-solvent. In other words, the two vehicles may effectively be extracted together by the anti-solvent to form a supercritical or near-critical solution.

In the case where the first vehicle is less than substantially soluble in the anti-solvent fluid (for instance, it has a solubility of 2 or even 1 mole % or less in the anti-solvent), the present invention can make use of a "dilution" of the target solution/suspension in a relatively large amount of the second vehicle; in this case there is therefore preferably an excess of the second vehicle over the first, at their point of contact with the anti-solvent fluid.

The method of the invention can retain all the advantages of the methods described in WO-95/01221 and WO-96/

00610. It can provide the opportunity for manufacturing dry particulate products with highly controlled particle size, shape and other physicochemical characteristics.

The simultaneous co-introduction of the target solution/suspension, the second vehicle and the anti-solvent fluid, into the particle formation vessel, allows a high degree of control over operating parameters such as temperature, pressure and fluid flow rates, at the exact point when the fluids come into contact with one another and hence at the point of actual particle formation. Importantly, the anti-solvent acts both to disperse and to extract the two vehicles, as well as to ensure their thorough mixing—because of this, controlling the relative flow rates of the fluids into the particle formation vessel allows accurate control over the size of the fluid elements formed on dispersion of the vehicles, and hence of the particles formed substantially simultaneously by extraction of the vehicles into the anti-solvent fluid.

The target substance may be any substance which needs to be produced in particulate form. Examples include pharmaceuticals; pharmaceutical excipients such as carriers; dyestuffs; foodstuffs; coatings; agrochemicals; products of use in the ceramics, explosives or photographic industries; etc. . . . It may be organic or inorganic, monomeric or polymeric. It may in particular be a hydrophilic material such as a sugar, protein or enzyme.

In a preferred embodiment of the invention, the target substance is for use in or as a pharmaceutical or pharmaceutical excipient.

The target substance will typically (although not always) either be or comprise a substance which is soluble or substantially soluble only in solvents which are themselves substantially insoluble in the chosen anti-solvent fluid. It may be a substance which, though soluble in an appropriate anti-solvent-soluble vehicle, would be in some way incompatible with that vehicle. It is preferably, however, soluble or substantially soluble in the first vehicle, preferably having a solubility in it of $10^{-4}$ mole % or greater. It may even be soluble, at least to a degree, in both the first and the second vehicles.

The target substance may be in a single or multi-component form (eg, it could comprise an intimate mixture of two materials, or one material in a matrix of another, or one material coated onto a substrate of another, or other similar mixtures). The particulate product, formed from the target substance using the method of the invention, may also be in such a multi-component form—such products may be made from solutions/suspensions containing only single component starting materials, provided the solutions/suspensions are co-introduced with the anti-solvent fluid in the correct manner. The particulate product may comprise a substance formed from an in situ reaction (ie, immediately prior to, or on, dispersion by the anti-solvent) between two or more reactant substances each carried by an appropriate vehicle.

The method of the present invention is particularly suitable for co-precipitating two or more target substances, such as for example two pharmaceuticals intended for co-administration, or a pharmaceutical together with a polymer carrier matrix (many such polymers are water soluble, and the present invention allows the use of an aqueous first vehicle even though water is insoluble in, for instance, the common anti-solvent supercritical carbon dioxide). To perform such co-precipitations, target substance(s) may be carried in the second vehicle and/or the anti-solvent fluid, as well as in the first vehicle.

The anti-solvent fluid is preferably a supercritical fluid. It may for instance be carbon dioxide, nitrogen, nitrous oxide, sulphur hexafluoride, xenon, ethylene, chlorotrifluoromethane, ethane, trifluoromethane or a noble gas such as helium or neon, in an appropriate condition with respect to its critical temperature and pressure. A particularly preferred anti-solvent is carbon dioxide, more preferably supercritical carbon dioxide, due to its relatively low cost, toxicity, flammability and critical temperature.

It must be capable of acting as an anti-solvent for the target substance. Therefore, although it must be miscible or substantially miscible with the second vehicle so that it can extract the vehicle mixture, it must not at that point extract or dissolve the target substance as particles are formed. In other words, it must be chosen so that the target substance is for all practical purposes (in particular, under the chosen operating conditions and taking into account any fluid modifiers present) insoluble or substantially insoluble in it. Preferably the target substance is less than $10^{-3}$ mole %, more preferably less than $10^{-5}$ mole %, soluble in the anti-solvent fluid.

The anti-solvent fluid may optionally contain one or more modifiers, for example water, methanol, ethanol, isopropanol or acetone. A modifier (or co-solvent) may be described as a chemical which, when added to a fluid such as a supercritical or near-critical fluid, changes the intrinsic properties of that fluid in or around its critical point, in particular its ability to dissolve other materials. When used, a modifier preferably constitutes not more than 40 mole %, more preferably not more than 20 mole %, and most preferably between 1 and 10 mole %, of the anti-solvent fluid.

The choice of first and second vehicles in any particular case will depend on the nature of the target substance and the anti-solvent fluid, and on other practical criteria including those governing the desired end product. Either vehicle may comprise a mixture of two or more fluids which together have the necessary characteristics (such as solubility, miscibility and polarity) vis-a-vis the target substance and the other fluids involved. Alternatively, each of the vehicles may comprise a single fluid material rather than a mixture.

The choice of a suitable combination of anti-solvent fluid, modifier (where desired) and vehicles for any desired product will be well within the capabilities of a person of ordinary skill in the art.

Examples of suitable immiscible first/second vehicle pairs include water and higher (ie, $C_4$ or greater) alcohols such as 1-butanol; water and ethyl acetate; methanol and higher (ie, $C_5$ or greater) alkanes (including cycloalkanes) such as n-pentane, n-octane, hexane and cyclohexane; DMF (dimethyl formamide) and higher alkanes; DMSO (dimethyl sulphoxide) and higher alkanes; ethyl ether and DMSO; ethylene glycol and haloalkanes such as dichloromethane or 1,2-dichloroethane; glycerol and 3-pentanone; glycerol and ethyl acetate; 2-methoxyethanol and tetradecane; ethylformamide and hexane; 1-amino-2-propanol and isopropyl ether; 2-aminoethanol and dichloromethane; 2-aminoethanol and ethyl ether; 1,4-butanediol and butyl acetate; and water and dichloromethane. This list is clearly not exhaustive.

In the method of the invention, the target substance and the first vehicle may be substantially polar, and the second vehicle substantially non-polar. In contrast, a substantially non-polar substance may be dissolved in a substantially non-polar first vehicle, the second vehicle then being substantially polar. These two sets of conditions are of particular use when the second vehicle acts as an anti-solvent for the target substance, ie, when the target substance carried in the first vehicle is insoluble, or substantially so, in the second vehicle.

In such a case, if the first and second vehicles are not completely immiscible with one another, the second vehicle can help to cause precipitation of the target substance on contact with the target solution/suspension. The second vehicle may then contain a "seed" of the target substance, or indeed of any other suitable material (insoluble in the second vehicle), to induce nucleation of the target substance when the second vehicle comes into contact with the target solution/suspension. The seed may be, for example, a pharmaceutically acceptable carrier where the target substance is a pharmaceutical, or it may itself be a pharmaceutically active material, to be coated with a substance, such as a taste-masking agent, which is precipitated out of the first vehicle onto the seed.

When carrying out this version of the invention, the various fluids should be introduced into the particle formation vessel in such a way that the second vehicle and the target solution/suspension contact one another before, and preferably immediately before, their contact with the anti-solvent fluid. The target solution/suspension should also, generally, be highly saturated. The second vehicle, when it contacts the target solution/suspension, dramatically increases the supersaturation ratio of the resultant mixture, causing the formation of embryos or nucleation sites which can act as centres of crystallisation for the target substance. After and preferably immediately after this, the mixture (containing growing particle embryos) is dispersed by the anti-solvent fluid, and simultaneously the two vehicles are rapidly extracted into the anti-solvent, leading to the formation of a dry particulate product. This allows a high level of control over the growth of the particles and hence over their ultimate physicochemical characteristics.

As mentioned previously, if the first vehicle is less than substantially soluble in the anti-solvent fluid, there is preferably an excess of the second vehicle at the point of its contact with the first. This can be achieved, for instance, by appropriate selection of flow rates for the two vehicles on their introduction into the particle formation vessel. An excess of the second vehicle over the first can also be desirable in other cases, for instance when the two vehicles are immiscible in most but not all proportions.

Generally speaking the relative amounts of first and second vehicles used will depend on the natures of all the fluids involved, the operating conditions, the nature of the target substance and the desired product characteristics. The molar ratio of the two vehicles at the point of particle formation may range, for instance, between 1:99 and 99:1. It must of course be chosen so that the two vehicles are still extractable, together, into the anti-solvent fluid so it will depend in particular on the solubilities of the vehicles in the anti-solvent under the chosen operating conditions. Ideally it is chosen so that, under the operating conditions used, the target solution/suspension and the second vehicle form a single phase mixture at the point of particle formation.

For an excess of the second vehicle, the molar ratio of the first to the second vehicle may be less than 1:1.5 (for instance, between 1:100 and 1:1.5), preferably less than 1:4, more preferably less than 1:6, most preferably less than 1:9 or 1:10 or 1:20.

It may also be desirable to use the minimum possible amount of the first vehicle to solvate the target substance so as to create a single phase solution.

The amounts of the vehicles used, and their relative flow rates, may also depend on whether it is intended that some of the vehicle(s) remain in the final particulate product. For instance, if the first vehicle were water, then the amount used could affect whether the target substance were precipitated in an anhydrous form, or in the form of its monohydrate, dihydrate, or whatever. Thus, the concentration of the first, or indeed the second, vehicle in the eventual mixture of vehicles may be used to control "doping" of the final particulate product with vehicle "impurities". The invention allows a high degree of control over the residual vehicle content of the product.

In certain cases, the amount of the first vehicle (for instance, water) used may also determine which crystalline form of the target substance is formed.

When carrying out the present invention, the conditions in the particle formation vessel must generally be such that the anti-solvent fluid, and the supercritical or near-critical solution which is formed when it extracts the two vehicles, both remain in the supercritical/near-critical form whilst in the vessel. For the supercritical/near-critical solution, this means that at least one of its constituent fluids (usually the anti-solvent fluid, which in general will be the major constituent of the mixture) should be in a supercritical or near-critical state at the time of particle formation. There should at that time be a single-phase mixture of the two vehicles and the anti-solvent fluid, otherwise the particulate product might be distributed between two or more fluid phases, in some of which it might be able to redissolve. This is why the anti-solvent fluid needs to be miscible or substantially miscible with at least the second vehicle.

Provided such conditions are applied, extraction of the vehicles is then effectively immediate when the target solution/suspension and second vehicle contact the anti-solvent. This allows the rapid formation of a pure, dry particulate product.

The operating temperature and pressure (ie, within the particle formation vessel) and the fluid flow rates needed to achieve this situation will depend on the natures of the fluids involved (in particular, their $P_c$ and $T_c$ values and their solubility and miscibility curves) but will also be affected by the characteristics desired of the particulate end product, for instance a high yield, or a certain particle size or shape or purity. If for instance the objective is a high product yield, then it might be preferable (when using a supercritical fluid anti-solvent) to maintain the pressure inside the particle formation vessel substantially in excess of the anti-solvent $P_c$ (for instance, between 4 and 9 times the $P_c$, say 100–300 bar for carbon dioxide) whilst the temperature is only slightly above the $T_c$ (for instance, between 1.01 and 2 times the $T_c$, say 40–60° C. for carbon dioxide).

If however the objective is smaller particles with a narrower size distribution, then (subject to the constraints imposed by the relevant $P_c$ and $T_c$ values) higher temperatures (eg, between about 2 and 4 times the $T_c$) may be preferred for the anti-solvent fluid, since they lower its viscosity and can hence improve its dispersing effect on the other fluids.

For some target substances, the product morphology can be heavily influenced by the state of the anti-solvent fluid. For example, nicotinic acid particles prepared using the method of the invention, with supercritical carbon dioxide as the anti-solvent, will precipitate as rounded particles of about 100 micron average diameter when the anti-solvent is in a liquid-like phase (ie, at a relatively high pressure and low temperature with respect to its critical point), but as well-faceted, octagonal particles with an average diameter of less than 10 micron when the anti-solvent is more gas-like (higher temperature, lower pressure).

A major advantage of the present invention is therefore its versatility, different product characteristics being achievable simply by varying the operating conditions.

The flow rate of the anti-solvent fluid relative to those of the other fluids, and its pressure and temperature, should be sufficient to allow it to accommodate the vehicles (generally, the vehicles will represent no more than around 5% v/v of the anti-solvent fluid), so that it can extract them and hence cause particle formation. The anti-solvent flow rate should therefore generally be higher than those of the other fluids—typically, the ratio of the target solution/suspension flow rate to the anti-solvent flow rate (both measured at or immediately prior to the two fluids coming into contact with one another) will be 0.001 or greater, preferably between 0.01 and 0.2, more preferably between about 0.03 and 0.1.

The flow rate of the anti-solvent fluid, relative to those of the other fluids, is particularly important because it acts to disperse the two vehicles. Its flow rate can therefore affect the size and size distribution of fluid elements caused by the dispersion, and hence of the particles formed by extracting the vehicles from those fluid elements; a higher flow rate is preferred so as to generate correspondingly smaller fluid elements with a narrower particle size distribution.

The anti-solvent flow rate will also generally be chosen to ensure an excess of the anti-solvent over the two vehicles when the fluids come into contact, to minimise the risk of the vehicles re-dissolving and/or agglomerating the particles formed. At the point of extraction of the two vehicles they may together constitute between 1 and 80 mole %, preferably 50 mole % or less or 30 mole % or less, more preferably between 1 and 20 mole % and most preferably between 1 and 5 mole %, of the fluid mixture formed.

Because the present invention is a modified version of that disclosed in WO-96/00610, technical features of the processes described in WO-96/00610 and its precursor WO-95/01221 (and also in the later but related document WO-98/36825) can apply also to the present invention. The three earlier documents are therefore intended to be read together with the present application.

In particular, the fluids are preferably co-introduced into the particle formation vessel in the manner described in WO-95/01221, ie:

(a) the anti-solvent fluid and the target solution/suspension both enter the vessel at the same or substantially the same point, which is the same or substantially the same as the point at which they meet; and (b) the fluid inlet used to co-introduce the fluids is arranged so that the mechanical energy (typically the shearing action) of the anti-solvent flow can facilitate intimate mixing of the fluids and also disperse them, and so that the anti-solvent can simultaneously extract the vehicles, at the point where the fluids meet.

The vessel temperature and pressure are ideally controlled so as to allow particle formation to occur at or substantially at the point where the vehicle mixture meets the anti-solvent fluid.

The fluid inlet may be of the type which allows "pre-filming" or "sheathing" of at least one of the fluids to occur, immediately prior to its dispersion by an impinging flow of another fluid introduced through the inlet means. For instance, the inlet means can be used to cause pre-filming of the target solution/suspension, and/or of the second vehicle, immediately prior to their dispersion by the anti-solvent fluid. This means that the dimensions of the inlet passages of the inlet means, and the relative positions of their outlets, must be such that a fluid entering through one passage is formed, as it reaches the outlet of that passage, into a thin film or sheath, by its contact with, say, the lip of an adjacent passage outlet. This film or sheath can then be stretched, and ultimately dispersed into separate fluid elements, when it comes into contact with an oncoming stream of a fluid in another inlet passage. Clearly, the thickness of the film or sheath, and hence the sizes of the fluid elements formed on dispersion, will depend to a large extent on the relative flow rates of the fluids, and also on the inlet passage dimensions.

In one embodiment of the invention, the anti-solvent fluid and the target solution/suspension, and preferably also the second vehicle, are co-introduced into the particle formation vessel with concurrent directions of flow, preferably with coaxial or substantially coaxial flows, such as using a multi-passage coaxial nozzle. Such a nozzle has an outlet end communicating with the interior of the particle formation vessel, and two or more coaxial, conveniently concentric, passages which terminate adjacent or substantially adjacent one another at the outlet end, at least one of the passages serving to introduce a flow of the anti-solvent fluid into the particle formation vessel, at least one of the passages serving to introduce a flow of the target solution/suspension and preferably at least one of the passages serving to introduce a flow of the second vehicle. The three fluids may then be allowed to meet only at or immediately before the outlet end of the nozzle.

Aspects of the construction and geometry of such a coaxial nozzle may be as described in WO-95/01221 or WO-96/00610. For instance, the opening at the outlet end (tip) of the nozzle will preferably have a diameter in the range of 0.005 to 5 mm, more preferably 0.05 to 2 mm, most preferably between 0.1 and 0.5 mm, for instance about 0.1, 0.2, 0.3 or 0.35 mm. The angle of taper of the outlet end (with respect to the longitudinal axis of the nozzle) will depend on the desired velocity of the fluids introduced through the nozzle; a change in the angle may be used, for instance, to increase the velocity of the anti-solvent fluid and hence to increase the amount of its physical contact with the target solution/suspension and the second vehicle, leading to more efficient fluid mixing. Typically, the angle of taper will be in the range 10° to 60°, preferably between 10° and 50°, more preferably between 20° and 40°, and most preferably about 30°. Alternatively, the outlet need not be tapered at all.

The nozzle may be made of any appropriate material, for example stainless steel. It may have three coaxial passages, an inner, an intermediate and an outer, to allow both vehicles, and the anti-solvent fluid, to be introduced separately into the particle formation vessel. However, the nozzle may have any appropriate number of coaxial passages, some of which may be used to introduce additional reagents. One or more of the passages may be used to introduce two or more fluids at the same time, and the inlets to such passages may be modified accordingly.

As an example of this, the target solution/suspension may be introduced through one nozzle passage, whilst the anti-solvent fluid and the second vehicle are introduced together through another. Mixing of the two vehicles then occurs simultaneously with their dispersion and extraction by the anti-solvent. This may be effected using a two-passage nozzle or, using a nozzle having three or more passages, the target solution/suspension may be introduced between an inner and an outer flow of the anti-solvent/second vehicle mixture, which improves dispersion and mixing by exposing both sides of the target solution/suspension to the anti-solvent and second vehicle.

The internal diameters of the coaxial passages may be chosen as appropriate for any particular case. Typically, for a three-passage nozzle, the ratio of the internal diameters of the outer and the inner passages may be in the range from 2 to 10, preferably between 2 and 5, more preferably between 3 and 4. The ratio of the internal diameters of the outer and intermediate passages may be in the range from 1.01 to 5, preferably between 1.2 and 3. For a two-passage nozzle, the ratio of the internal diameters of the outer and inner passages may be in the range from 1 to 10, preferably between 2 and 6, more preferably between 2 and 4.

The outlets of two or more of the passages may be relatively staggered along the longitudinal axis of the nozzle, ie, one passage may terminate slightly upstream or downstream, in use, of another. The distance between the passage outlets should be sufficient to ensure, within the nozzle, good physical contact between and efficient mixing of the fluids introduced through the relevant passages, and so may be affected by other operating conditions such as pressure, temperature, fluid densities and viscosities and their flow rates. Typical values are between about 0.05 and 10 mm, preferably between about 0.05 and 5 mm, more preferably between about 0.5 and 3.5 mm, most preferably about 3 mm.

As an example, the outlet of an inner passage may be located slightly upstream of that of a surrounding passage, to allow a degree of internal mixing between fluids introduced through the two passages. This may be useful for instance when the target substance is insoluble in the second vehicle, the internal mixing resulting in a degree of initial particle precipitation. The target solution/suspension and the second vehicle are introduced through the inner passage and surrounding passage in question. The anti-solvent fluid may then be introduced through a passage surrounding the two already mentioned, and will contact the mixture, causing dispersion and extraction to occur, downstream of the initial point of mixing. The relative flow rates of the fluids will determine how soon after mixing the two vehicles will be dispersed by the anti-solvent; typically, as explained above, very short time intervals will be desired.

A nozzle having more than three coaxial passages may of course be used in this version of the invention. For instance, a nozzle having four or more passages may be used to introduce the target solution/suspension and the second vehicle (and preferably to cause their pre-filming), between an inner and an outer flow of the anti-solvent fluid. Again, the two passages carrying the target solution/suspension and the second vehicle may have staggered outlets, to allow pre-mixing to take place within the nozzle.

A fluid inlet means of the type described in WO-98/36825 (which provides two impinging flows of anti-solvent fluid) may also be used in the method of the present invention.

Control of parameters such as size, size distribution, shape and crystalline form in the particulate product will be dependent upon the operating conditions used when carrying out the method of the invention. Variables include the flow rates of the anti-solvent fluid and/or the target solution/suspension and/or the second vehicle, the relative amounts of the two vehicles, the concentration of the target substance in the first vehicle, and (as discussed above) the temperature and pressure inside the particle formation vessel. The method of the invention preferably involves controlling one or more of these variables so as to influence the physico-chemical characteristics of the particles formed.

The fluid flow rates, together with the concentration of the target substance in the first vehicle, are ideally selected so as to minimise the risk of particle precipitation in, and hence blockage of, the fluid inlet or other upstream apparatus parts. For the same reason, back-flow of the anti-solvent fluid, into the supply line for the target solution/suspension or the second vehicle, is also ideally reduced or eliminated. This may be done for instance by installing a one-way valve in the target solution/suspension supply line and/or in the second vehicle supply line, upstream of and preferably immediately before the point of contact between the relevant fluid(s) and the anti-solvent. Instead or in addition, the supplied pressure of the target solution/suspension and/or of the second vehicle, to the particle formation vessel, may be maintained in excess of that of the anti-solvent fluid. It is also preferable to maintain the temperature of either or both of those two fluids, prior to their introduction into the particle formation vessel, in excess of that of the anti-solvent fluid.

The fluids are ideally introduced into the particle formation vessel with a smooth, continuous and preferably pulse-less or substantially pulse-less flow. This again helps prevent draw-back of fluids. Conventional apparatus may be used to ensure such fluid flows.

The densities of the fluids used will depend on the operating conditions; in the case where supercritical carbon dioxide is used as the anti-solvent fluid, its density might typically be between 0.1 and 0.9 g/ml.

The method of the invention preferably additionally involves collecting the particles following their formation, more preferably in the particle formation vessel itself. The method may also involve recovering the supercritical or near-critical solution formed on extraction of the vehicles into the anti-solvent fluid, separating the components of the solution and re-cycling one or more of those components for future use.

The method is preferably carried out in a substantially continuous, as opposed to batch-wise, manner.

The present invention will now be described, by way of example only, with reference to the accompanying illustrative drawings, in which.

DETAILED DESCRIPTION

Figure 1:
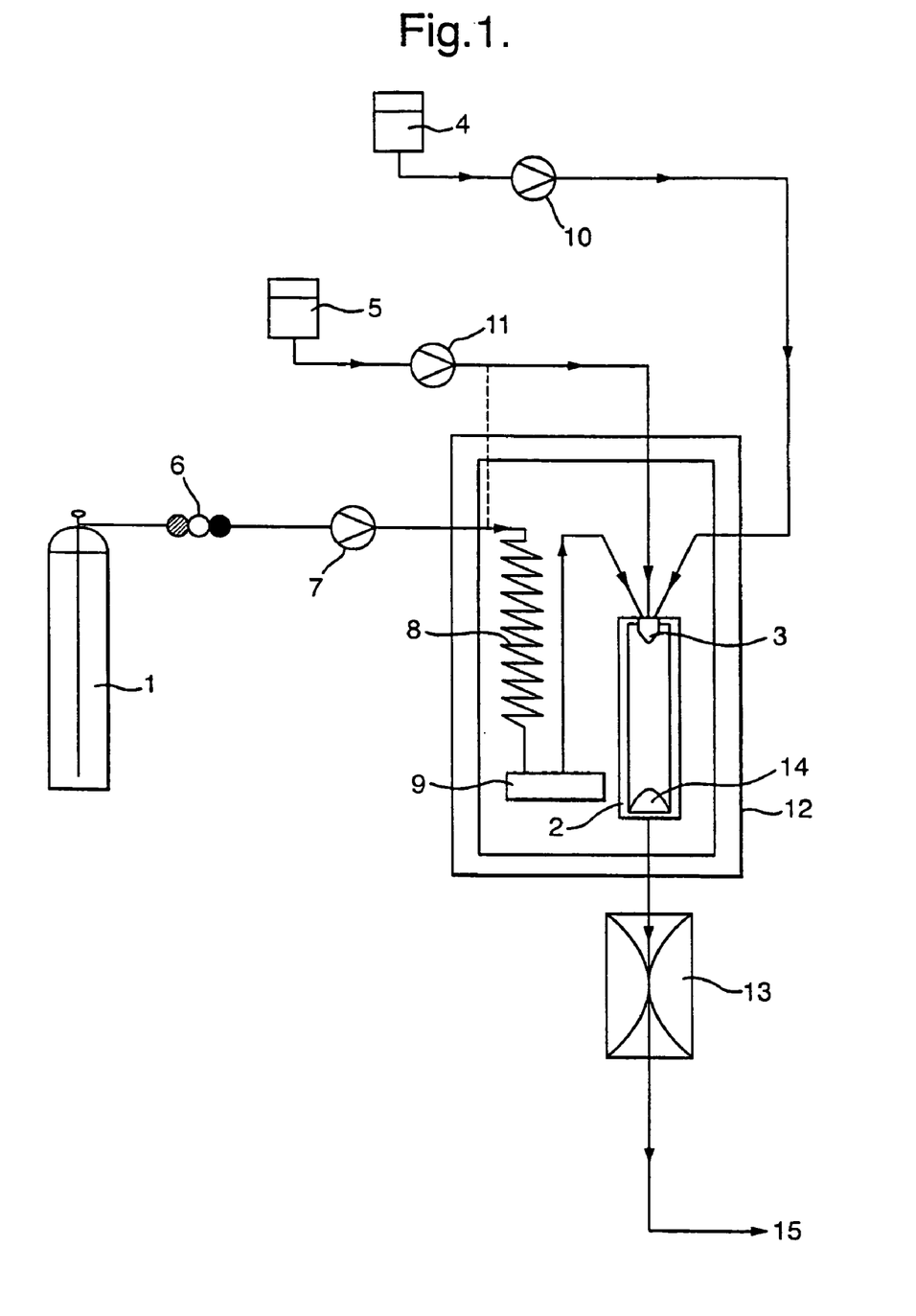
FIG. 1 illustrates schematically how a method in accordance with the present invention may be carried out.

Referring firstly to FIG. 1, the apparatus illustrated may be used to carry out a method in accordance with the present invention, as follows.

A supercritical or near-critical anti-solvent fluid 1 (such as supercritical carbon dioxide) is introduced into a particle formation vessel 2 via a suitable fluid inlet such as nozzle 3. Co-introduced with the anti-solvent, also via nozzle 3, are a solution or suspension 4 of a target substance in a first vehicle, and a second vehicle 5. In the case shown, the anti-solvent passes through a cooler 6, pump 7, heat exchanger 8 and pulse dampener 9; the target solution/suspension passes through pump 10 and the second vehicle passes through pump 11.

The temperature and pressure inside the vessel 2 are controlled by means of the surrounding oven 12 and the back pressure regulator 13, to ensure that supercritical or near-critical conditions are maintained throughout particle formation. Thus, the solution formed when the anti-solvent extracts the two vehicles is also present as a single-phase supercritical/near-critical fluid.

The particles formed on contact between the anti-solvent and the other fluids are collected in the retaining device (such as a filter) 14, and the fluids are vented at 15.

Figure 2:
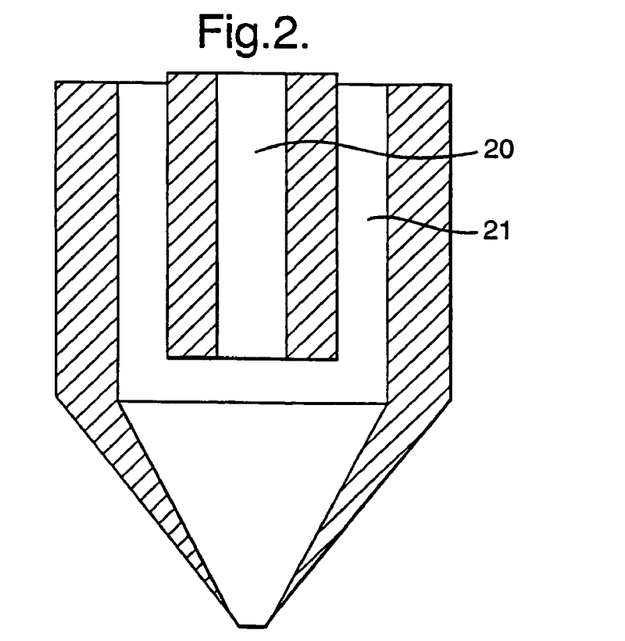
FIGS. 2–4 are longitudinal cross sections through nozzles which may be used in carrying out the methods of the invention.
Figure 3:
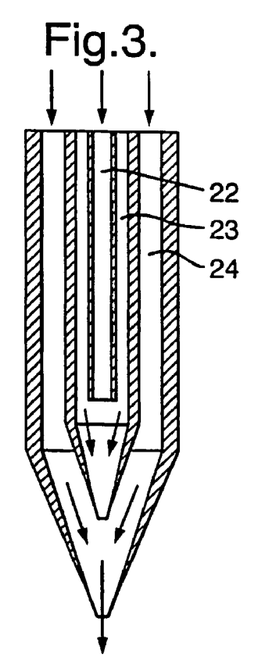
Figure 4:
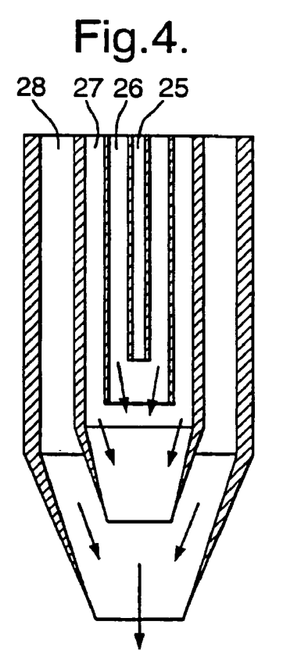

Suitable nozzles for use in the FIG. 1 apparatus are shown in FIGS. 2–4. In each case, the nozzle comprises two or more concentric, coaxial passages—two in the FIG. 2 nozzle, three in the FIG. 3 nozzle and four in the FIG. 4 nozzle. Also in each case, at least one inner nozzle passage terminates slightly upstream (in use) of the outlet of one of its surrounding passages.

The FIG. 2 nozzle, for instance, comprises an inner passage 20 and an outer passage 21 with respective internal diameters of 0.35 mm and 0.75 mm. A target solution/suspension may for instance be introduced through the inner passage and a mixture of an anti-solvent fluid and a second vehicle through the outer passage. The nozzle outlet diameter is 0.2 mm. Its central longitudinal axis is indicated by a dashed line.

The FIG. 3 nozzle comprises inner, intermediate and outer passages 22, 23 and 24 respectively. Inner passage 22 terminates upstream of the outlet of the intermediate passage 23, allowing a degree of internal mixing to occur between fluids introduced through those two passages, immediately before they contact a third fluid (eg, an anti-solvent fluid) introduced through the outer passage 24. The arrows indicate generally the directions of fluid flow through the in-use nozzle.

The FIG. 4 nozzle comprises four coaxial passages, 25–28, again with staggered outlets. It may be used, for instance, to introduce a target solution/suspension through passage 26, and a second vehicle through the surrounding passage 27, "sandwiched" between inner and outer flows of an anti-solvent fluid in passages 25 and 28.

EXPERIMENTAL EXAMPLES

Example 1

Using apparatus of the type illustrated in FIG. 1, and a three-passage nozzle of the type shown in FIG. 3, the method of the invention was used to co-precipitate two target substances, salmeterol xinafoate and paracetamol, to form an intimate mixture of the two pharmaceuticals.

The paracetamol was introduced in the form of a 1.5% w/v solution in a first vehicle (water), via the inner nozzle passage, with a flow rate of 0.04 ml/min. The salmeterol was introduced as a 0.5% w/v solution in a second vehicle, 1-butanol, through the intermediate nozzle passage, at a flow rate of 1 ml/min. The molar ratio of the two vehicles, water:1-butanol, was 0.17:0.83. A supercritical carbon dioxide anti-solvent was introduced, with a flow rate of 18 ml/min (measured at the pump head), through the outer nozzle passage.

Water and 1-butanol are immiscible, and of the two only 1-butanol is soluble in supercritical carbon dioxide under the operating conditions used.

The particle formation vessel was a 50 ml Keystone vessel, maintained throughout the experiment at 150 bar and 50° C. Under these conditions carbon dioxide is more liquid-like than gas-like in properties.

Figure 10:
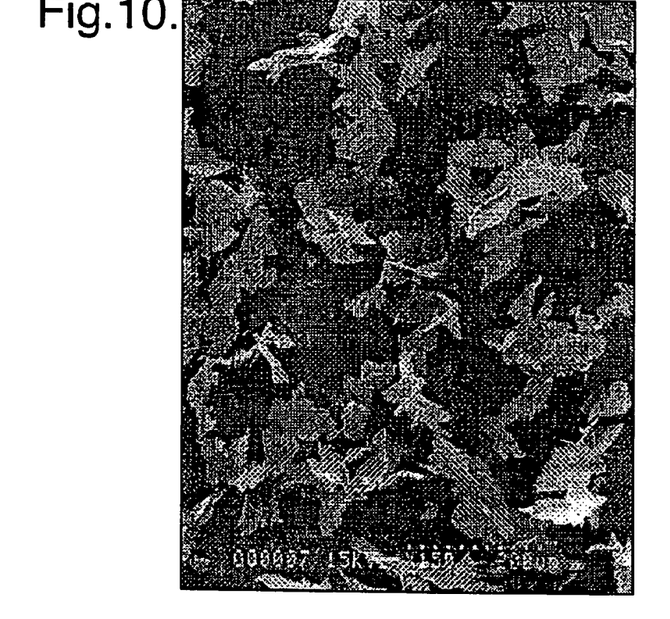
FIGS. 10 and 11 are scanning electron microscope (SEM) photographs of the products of Examples 1 and 2 respectively.

The product was a fine, free flowing, white powder, which was collected in the vessel and subsequently stored free from light and moisture. Its SEM photograph, taken at 150× magnification, is shown in FIG. 10.

Example 2

Example 1 was repeated but with a 0.2% w/v salmeterol xinafoate solution rather than 0.5% w/v.

Again, the product was a fine, free flowing white powder, in which HPLC analysis confirmed the presence of paracetamol.

Figure 5:
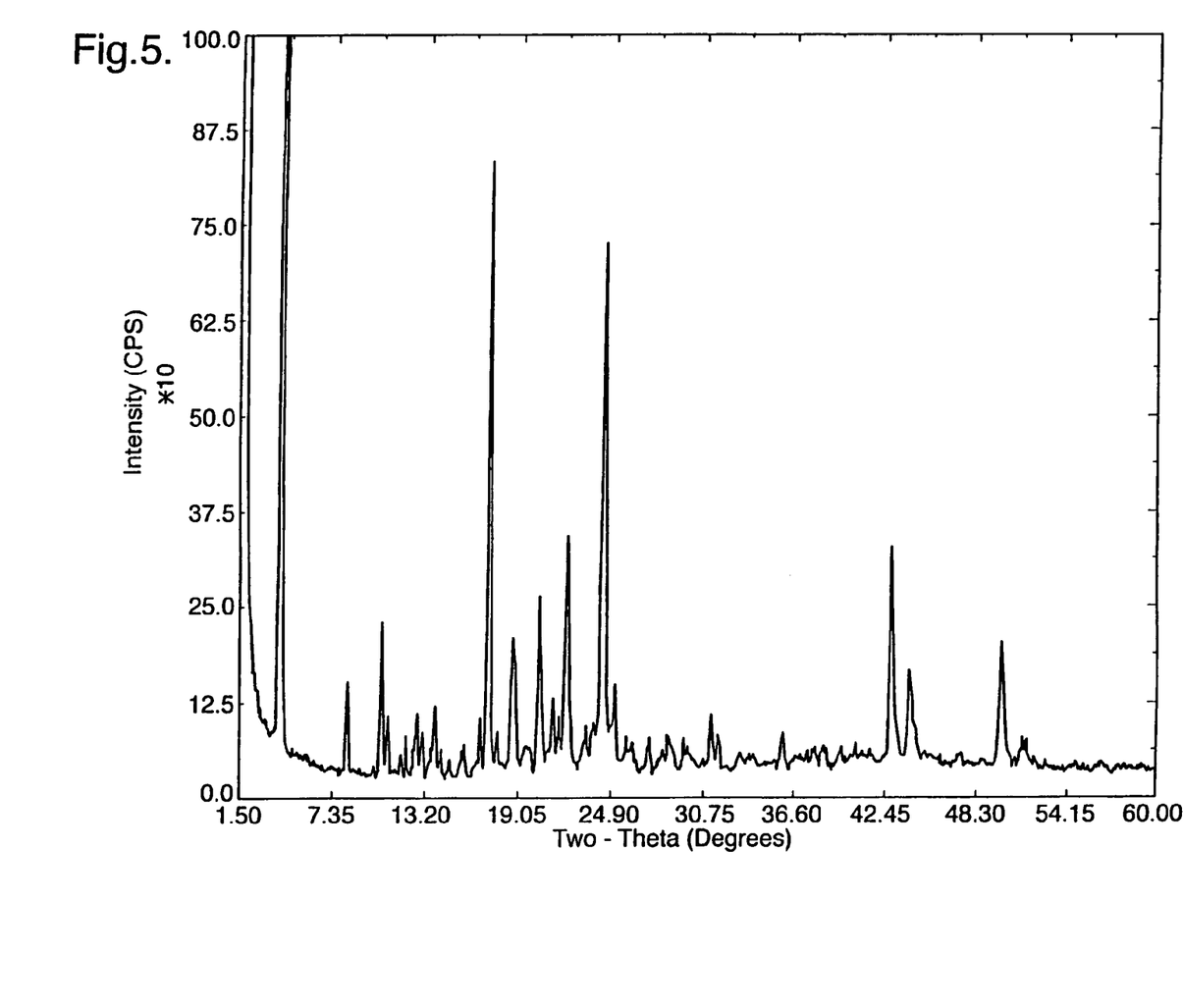
FIG. 5 is an X-ray powder diffraction profile for the product of Example 2 below.
Figure 6:
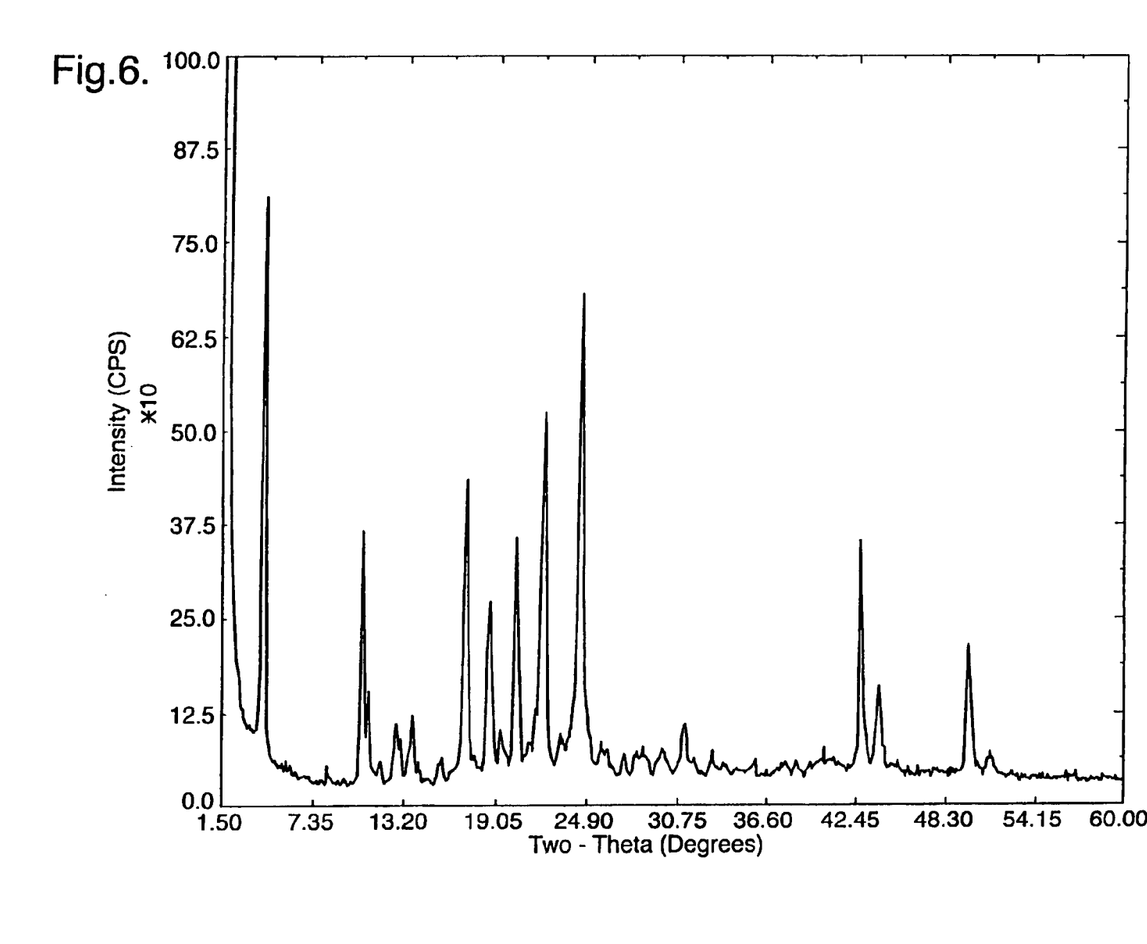
FIGS. 6 and 7 are X-ray powder diffraction profiles for pure salmeterol xinafoate and paracetamol respectively, for comparison with FIG. 5.
Figure 7:
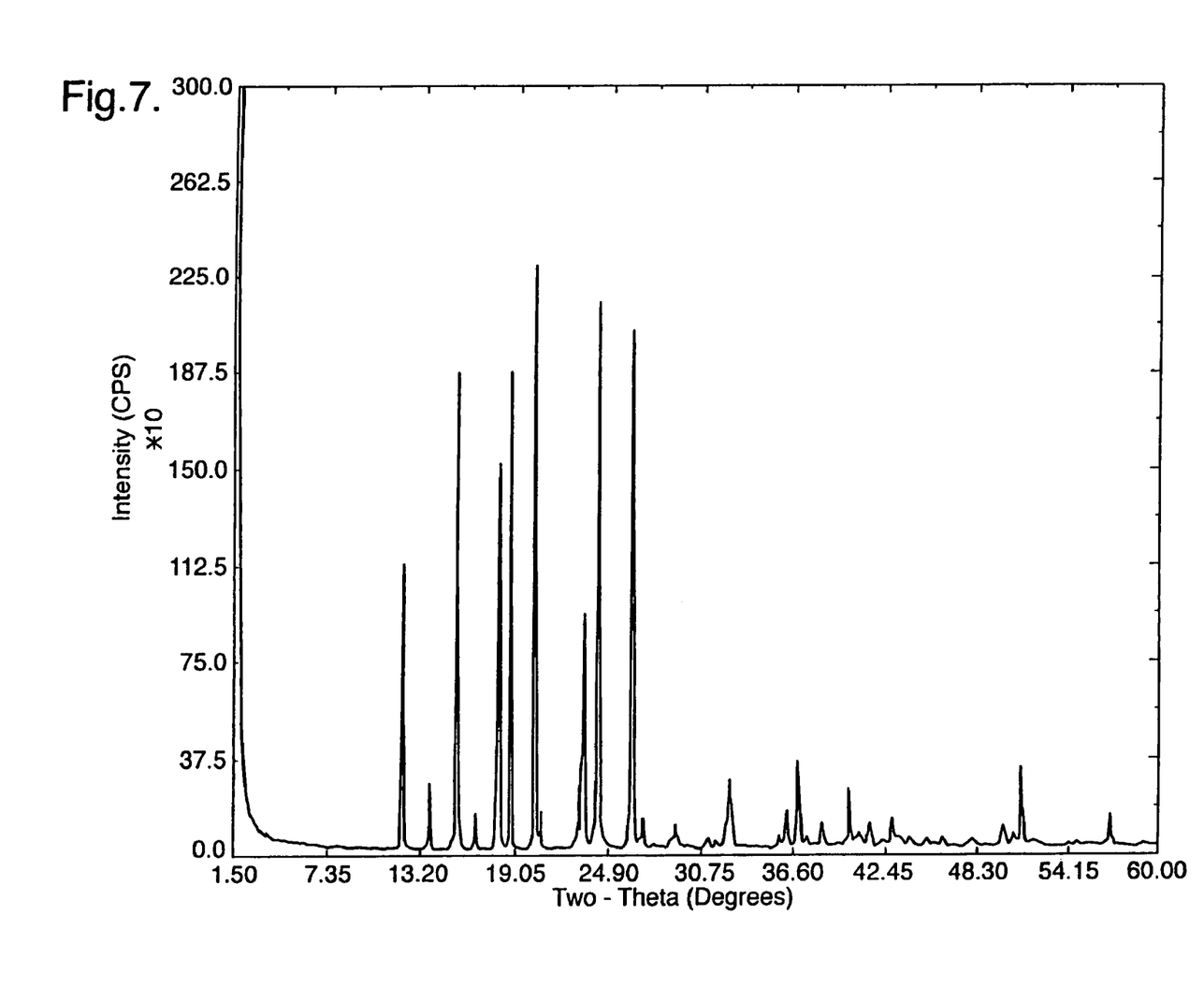

The X-ray powder diffraction profile for the product (FIG. 5) differed slightly from those obtained for pure salmeterol (FIG. 6) and pure paracetamol (FIG. 7), indicating that an intimate mixture had been formed between the two co-precipitated drugs.

Figure 8:
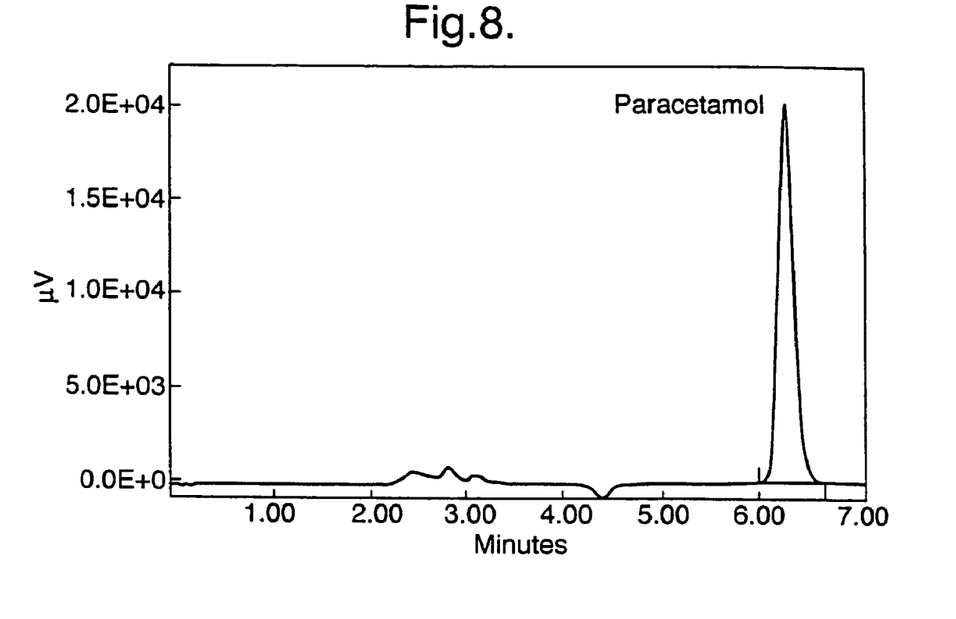
FIG. 8 is a high performance liquid chromatography (HPLC) chromatograph for the product of Example 2.
Figure 9:
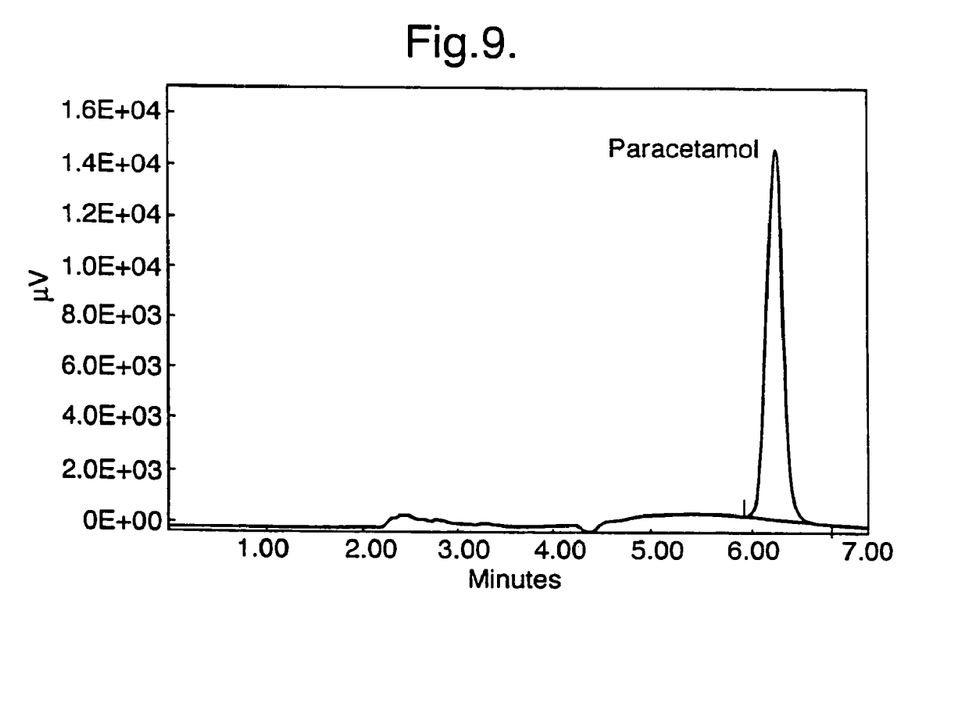
FIG. 9 is an HPLC chromatograph for a paracetamol calibration standard, for comparison with FIG. 8.

HPLC analysis of the product (FIG. 8) confirmed the presence of paracetamol in the powder mixture—a clear peak was produced at a similar retention time to that found for the paracetamol standard (FIG. 9).

Figure 11:
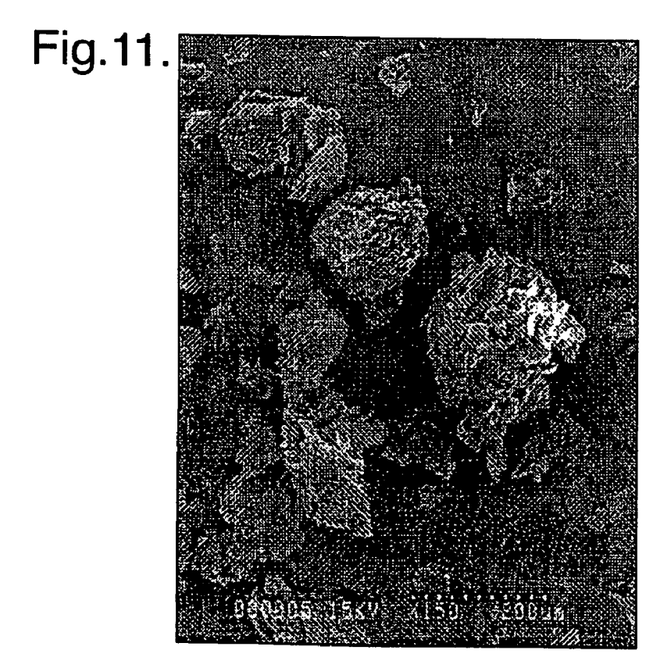

An SEM photograph of the product, taken at 150× magnification (FIG. 11), shows a considerable difference in crystal habit between the products of Examples 1 and 2. This change may be due to the lower salmeterol solution concentration and the resultant higher paracetamol concentration in the final product of Example 2.

Example 3

Again using apparatus of the type shown in FIG. 1, and a three-passage coaxial nozzle, paracetamol was co-precipitated with L-poly lactic acid (L-PLA) using dichloromethane (DCM) and ethylene glycol (EG) as the two vehicles. DCM and EG are immiscible at room temperature and are not expected to be miscible or to have a critical solution temperature below 75° C. (N. Godfrey, *Chemtech*, June 1972, pp 359–363), due to the difference in their miscibility numbers. Both vehicles are soluble in supercritical carbon dioxide over a wide range of pressures and temperatures.

A 1.5% w/v solution of L-PLA (Resomer 206) in DCM was introduced into the apparatus at a rate of 0.4 ml/min via the inner nozzle passage. Through the intermediate passage, a 6% w/v solution of paracetamol in EG was introduced at 0.1 ml/mn. The molar ratio of EG:DCM was 0.274:0.736. Both solution streams were mixed and dispersed with a supercritical carbon dioxide anti-solvent flowing through the outer nozzle passage at 30 ml/min (measured at the pump head). The particle formation vessel was a 50 ml high pressure vessel (Keystone) kept at 150 bar and 45° C. The nozzle outlet was 0.2 mm in diameter.

Figure 12:
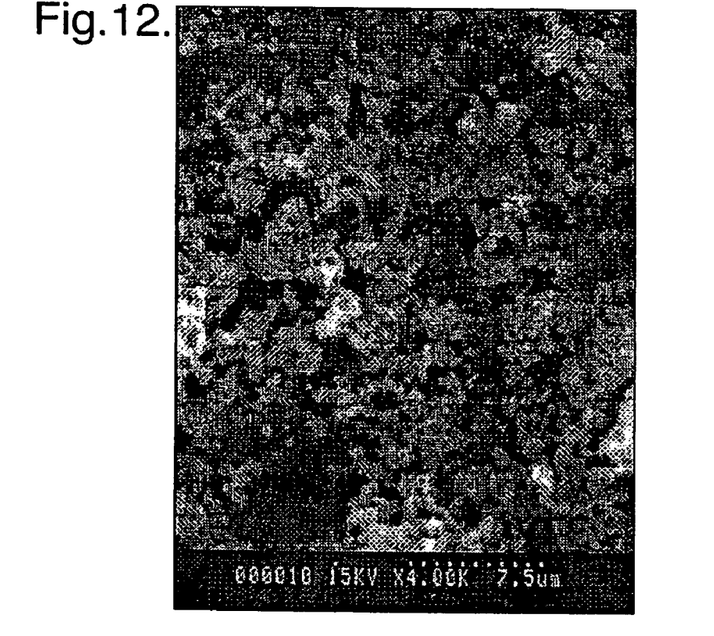
FIGS. 12 and 13 are SEM photographs of the products of Examples 3 and 4 respectively.

At the end of the experiment a fine, fluffy, easy-flowing white powder was collected and stored in a screw cap bottle for subsequent analysis. FIG. 12 is a SEM photograph of the product at 4000× magnification.

Example 4

Example 3 was repeated at a higher operating temperature, 60° C. All other experimental conditions were unchanged.

Figure 13:
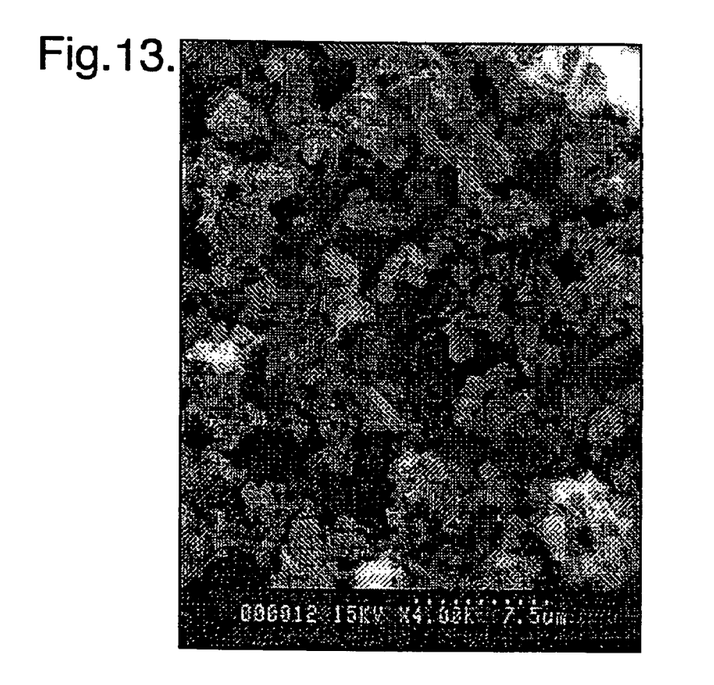

A similar powder product was obtained; its SEM photograph is shown in FIG. 13 (4000× magnification).

Figure 14:
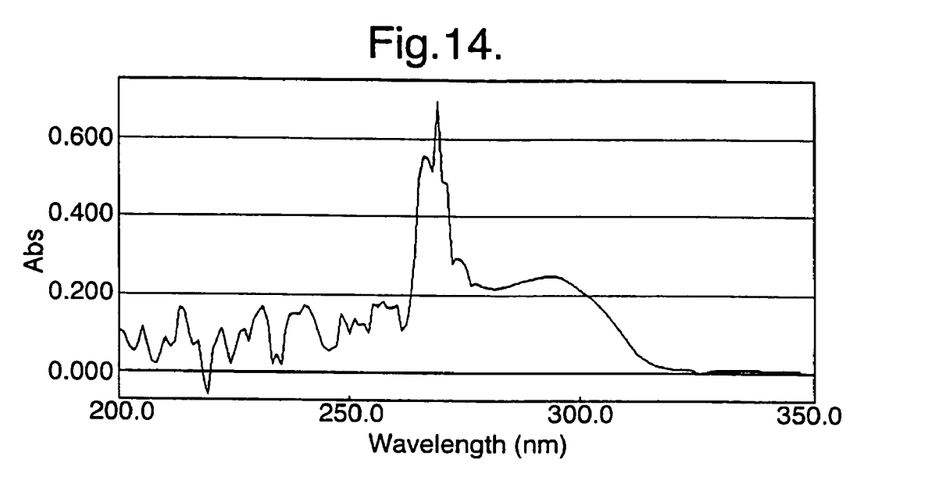
FIGS. 14 and 15 are UV absorption spectra for, respectively, pure paracetamol and the paracetamol-containing product of Example 4.

To verify the presence and quantity of paracetamol in the product, spectroscopic absorption measurements were taken using an Ultrospec™ 4000 UV/V is spectrophotometer (Pharmacia Biotech). Pure paracetamol absorbs UV light at 268 nm (see the UV absorption spectrum shown in FIG. 14). This is a region of the spectrum in which L-PLA does not absorb.

Figure 15:
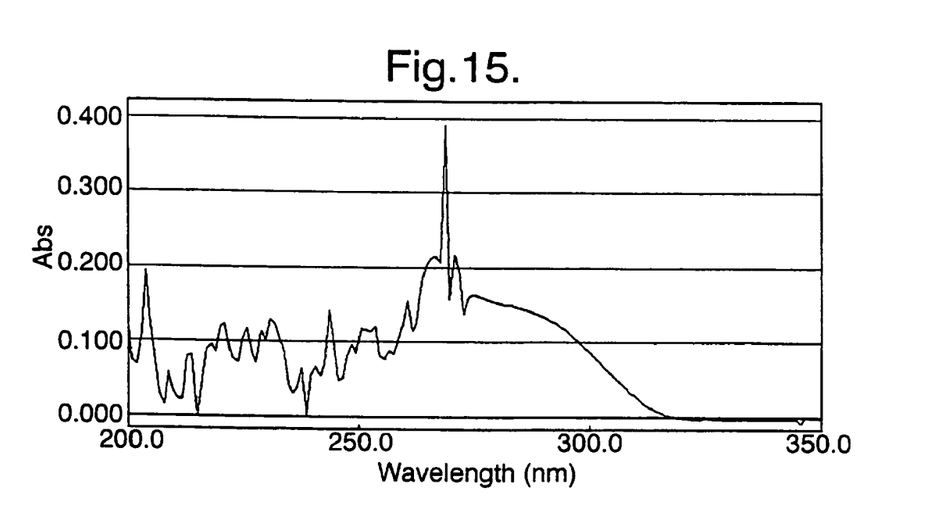

A 0.01 mg/ml DMF solution of the product was tested. This was expected to contain 50% w/w of paracetamol, in view of the quantities of drug and polymer introduced into the particle formation vessel, assuming no solute loss into the carbon dioxide anti-solvent. Its absorbance was found to be 0.213 (absorption spectrum shown in FIG. 15).

Figure 16:
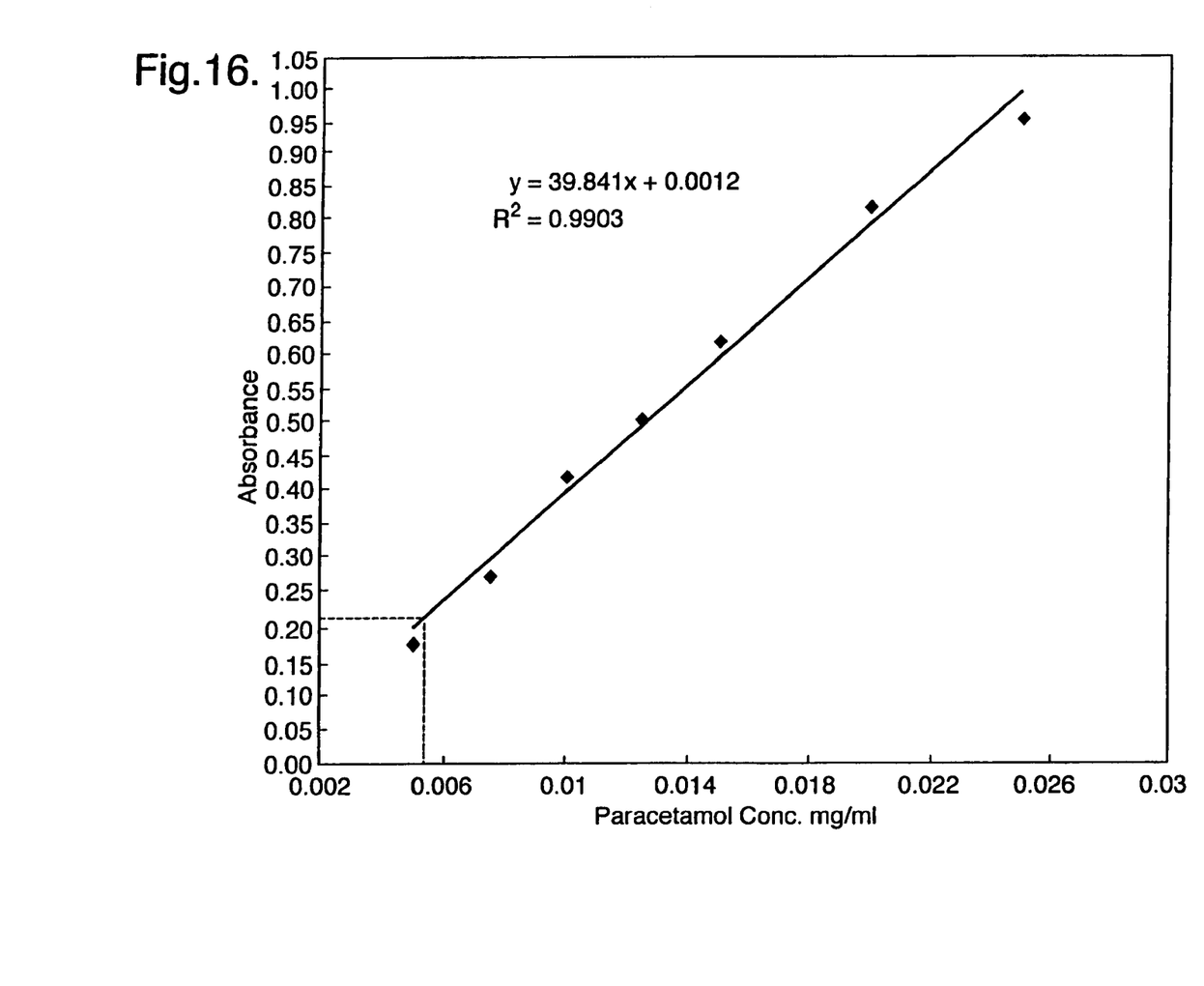
FIG. 16 shows the correlation between absorbance (268 nm) and concentration for standard paracetamol samples in DMF.

FIG. 16 shows the correlation between absorbance (268 nm) and concentration for standard paracetamol samples in DMF. Substitution of an absorbance value (y) of 0.213 into the equation shown on the graph gives a concentration (x) of 0.0053 mg/ml (dashed line in FIG. 16). This is very close to the theoretical value of 0.0050, indicating that the paracetamol introduced into the particle formation system has been almost fully retained and that neither the L-PLA nor the paracetamol is soluble in supercritical carbon dioxide under the working conditions used.

The invention claimed is:

1. A method for forming particles of a target substance, comprising:
    co-introducing into a particle formation vessel, the temperature and pressure in which are controlled, an anti-solvent fluid which is either a supercritical or a near-critical fluid, a first target substance in a first vehicle, and a second target substance in a second vehicle; and
    using the anti-solvent fluid to disperse the target substances in their respective vehicles and to extract the vehicles, substantially simultaneously and substantially immediately on introduction of the fluids into the particle formation vessel, wherein the second vehicle is immiscible with the first vehicle, and wherein contact between the first and second vehicles occurs a sufficiently short period of time before their dispersion by the anti-solvent fluid, and with sufficient physical mixing, as to allow only insignificant, if any, phase separation to occur between the two vehicles between their contact with one another and their dispersion, and wherein particle formation occurs upon extraction of the vehicles by the anti-solvent.

2. The method of claim 1, wherein at least one of the target substances is a pharmaceutical.

3. The method of claim 1, wherein the anti-solvent comprises supercritical carbon dioxide.

4. The method of claim 1, wherein at least one of the target substances is selected from the group consisting of salmeterol and paracetamol.

5. The method of claim 1, wherein the contact occurs within between about 0.001 seconds and about 10 seconds of the dispersion of the pharmaceutical and target substance.

6. The method of claim 1, wherein one of the vehicles is water and the other vehicle is a C4 or higher alcohol.

7. The method of claim 1, wherein one of the vehicles is methanol and the other vehicle is a C5 or higher alkane.

8. The method of claim 1, wherein one of the vehicles is ethylene glycol and the other vehicle is a haloalkane.

9. The method of claim 1, wherein the vehicles are selected from the group consisting of water and 1-butanol; water and ethyl acetate; methanol and n-pentane; methanol and n-octane; methanol and hexane; methanol and cyclohexane; DMF (dimethyl formamide) and a higher alkane; DMSO (dimethyl sulphoxide) and a higher alkane; ethyl ether and DMSO; ethylene glycol and dichloromethane; ethylene glycol and 1,2-dichloroethane; glycerol and 3-pentanone; glycerol and ethyl acetate; 2-methoxyethanol and tetradecane; ethylformamide and hexane; 1-amino-2-propanol and isopropyl ether, 2-aminoethanol and dichloromethane; 2-aminoethanol and ethyl ether; 1,4-butanediol and butyl acetate; and water and dichloromethane.

* * * * *